United States Patent [19]
Chester et al.

[11] Patent Number: 5,969,143
[45] Date of Patent: Oct. 19, 1999

[54] PYRIDINE/PICOLINE PRODUCTION PROCESS

[75] Inventors: Arthur Chester, Cherry Hill; Scott Han, Lawrenceville; Dominick N. Mazzone, Wenonah; Chaya R. Venkat, Princeton, all of N.J.

[73] Assignee: Mobil Oil Corporation, Fairfax, Va.

[21] Appl. No.: 09/002,363

[22] Filed: Dec. 31, 1997

[51] Int. Cl.⁶ .................. C07D 213/08; C07D 213/06; C07G 213/09
[52] U.S. Cl. ............................. 546/250; 546/251
[58] Field of Search ...................... 546/250, 251

[56] References Cited

U.S. PATENT DOCUMENTS

| | | | |
|---|---|---|---|
| 4,220,783 | 9/1980 | Chang et al. | 546/251 |
| 4,675,410 | 6/1987 | Feitler et al. | 546/251 |
| 4,866,179 | 9/1989 | Cheng et al. | 546/250 |
| 5,218,122 | 6/1993 | Goe et al. | 546/251 |
| 5,395,940 | 3/1995 | Angevine et al. | 546/250 |
| 5,780,635 | 7/1998 | Mcateer et al. | 546/251 |

OTHER PUBLICATIONS

J.Ian Grayson et al.Helvetica Chimica Acta, vol.67, pp. 2100–2110 (1984).

*Primary Examiner*—Alan L. Rotman
*Attorney, Agent, or Firm*—Peter W. Roberts; Malcolm D. Keen

[57] ABSTRACT

There is provided a high efficiency base synthesis process for shape selective production of pyridine and picoline products from ammonia and $C_{1-5}$ carbonyl compounds. The process includes reacting ammonia and at least one $C_{1-5}$ carbonyl reactant under suitable reaction conditions of temperature, pressure, and space velocity in the presence of a catalyst comprising a molecular sieve to produce a primary product comprising pyridine or picoline products and polyalkylpyridines or other higher molecular weight aromatic species, separating and collecting the pyridine or picoline products from the polyalkylpyridines or other higher molecular weight aromatic species, and circulating the polyalkylpyridines or other higher molecular weight aromatic species to the same or another catalyst under conversion conditions to yield additional pyridine or picoline products with substantially reduced amounts of polyalkylpyridines or other higher molecular weight aromatic species.

15 Claims, No Drawings

PYRIDINE/PICOLINE PRODUCTION PROCESS

BACKGROUND OF THE INVENTION

1. Field of the Invention

The invention relates to improvements in processes for shape selective preparation of aromatic hydrocarbon compounds. More specifically, the invention relates to improvements in processes for preparing nitrogen-containing aromatic hydrocarbons such as pyridines and picolines.

2. Description of the Prior Art

Pyridine is a six-membered heterocyclic aromatic compound with one nitrogen atom in the ring structure. It is an important chemical in the manufacture of agricultural chemicals, e.g., herbicides and pesticides, and pharmaceuticals, and is also useful as a solvent in the polymer and textile industries. Important derivatives of pyridine include, for example, nicotinic acid and nicotinamide (vitamins essential for human health), chlorpheniramine (an antihistamine), cetylpyridinium (a germicide and antiseptic), isoniazid (an important antitubercular drug), and Paraquat® (a herbicide).

Pyridine itself is a simple ring structure, and has only hydrogen atoms bonded to the structure. Pyridines having one methyl group attached to the ring structure are called methylpyridines or picolines, and they include 2- or α-picoline, 3- or β-picoline, and 4- or γ-picoline. Dimethylpyridines are called lutidines, and the 2,6- and 3,5-lutidines are readily obtainable. Trimethylpyridines are called collidines, with the 2,4,6-collidine or sym-collidine being the most common. See "Pyridine and Pyridine Derivatives," *Kirk-Othmer Encyclopedia of Chemical Technology*, Vol. 19, 3rd. Ed. (1982).

Pyridine and picolines can be obtained as by-products of the coal tar industry or coke manufacture. However, pyridine is found in only small amounts in coal tar, and a preferred method of obtaining pyridine is by chemical synthesis. Chemical synthesis typically relies on a catalytic gaseous reaction (condensation) between ammonia (or amines) and carbonyl compounds such as aldehydes or ketones. However, these chemical synthesis methods have historically suffered from disadvantages of low yields and poor selectivity, and short operation cycle and catalyst lifetime.

The term "base synthesis" is known and used in the field of pyridine chemistry to identify synthetic processes by which bases of pyridine and its alkylated derivatives are prepared by reacting aldehydes and/or ketones with ammonia in the gas phase using a heterogeneous catalyst. For example, the reaction of acetaldehyde with ammonia in the presence of heterogenous catalysts at about 350° C. to about 550° C. yields 2- and 4-methylpyridines (β- and γ-picolines). As another example, acetaldehyde, formaldehyde, can be reacted with ammonia to yield pyridine and 3-methylpyridine. Such pyridine synthesis methods are described, for example, in U.S. Pat. No. 4,675,410 to Feitler and U.S. Pat. No. 4,220,783 to Chang et al. which are each herein incorporated by reference.

Reaction of acetaldehyde or certain other low molecular weight aldehydes and ammonia either in the absence or presence of methanol and/or formaldehyde to yield pyridine and alkyl derivatives thereof has been carried out in the presence of amorphous silica-alumina composites containing various promoters. See, for example, U.S. Pat. Nos. 2,807,618 and 3,946,020. The yields of desired products using the latter catalysts have been poor. Alkylpyridines have also been synthesized, as reported in *Advances in Catalysis*, 18:344 (1968), by passing gaseous acetaldehyde and ammonia over the crystalline aluminosilicates NaX and H-mordenite. While initial conversion utilizing these materials as catalysts was high, catalyst deactivation by coking was rapid, providing a commercially unattractive system, characterized by poor catalytic stability.

Amorphous aluminosilicate catalysts provide a reasonable yield of pyridine at the beginning of the process; however, after repeated operation cycles some limitations appear which make these catalysts unacceptable from a commercial standpoint.

Synthetic crystalline zeolites having an intermediate pore size as measured by the Constraint Index of the zeolite being between 1 and 12, e.g., ZSM-5, have been found to provide commercially useful yields and product selectivities. U.S. Pat. No. 4,220,783 was pioneer in this discovery, teaching synthesis of pyridine and alkylpyridines by reacting ammonia and a carbonyl reactant which is an aldehyde containing 2 to 4 carbon atoms, a ketone containing 3 to 5 carbon atoms or mixtures of said aldehydes and/or ketones under effective conditions in the presence of a catalyst comprising a crystalline aluminosilicate zeolite having been ion exchanged with cadmium and having a silica to alumina ratio of at least about 12, and a Constraint Index within the approximate range of 1 to 12.

Use of a ZSM-5 catalyst component in a fluidized or otherwise movable bed reactor is taught in U.S. Pat. No. 4,675,410. U.S. Pat. No. 4,886,179 teaches synthesis of pyridine by reaction of ammonia and a carbonyl compound, preferably with added hydrogen, over catalyst comprising a crystalline aluminosilicate zeolite which has been ion exchanged with a Group VIII metal of the Periodic Table. The crystalline aluminosilicate zeolite has a silica to alumina mole ratio of at least 15, preferably 30 to 200, a Constraint Index of from 4 to 12, e.g., ZSM-5, and the process provides a high and selective yield of pyridine.

U.S. Pat. No. 5,013,843 teaches addition of a third aldehyde or ketone to a binary mixture of aldehydes and/or ketones used in preparing mixtures of pyridine and alkyl-substituted pyridines in large scale continuous processes. In a preferred system, propionaldehyde is added to a binary mixture of acetaldehyde and formaldehyde to produce beta-pyridine and pyridine. The catalyst for this process is a crystalline aluminosilicate zeolite in the acidic form having a Constraint Index of from 1 to 12, e.g., ZSM-5.

U.S. Pat. No. 5,218,122 to Goe et al. relates to a process for base synthesis over a modified catalyst containing tungsten, zinc, or tin, and a constraint index of about 1 to 12.

These crystalline catalysts have been provided in an attempt to improve the performance of amorphous catalysts. However, the yield of pyridine, and selectivity operation life, and restorability of the catalyst after regeneration still have not been satisfactory. Specifically, the yield of pyridine is low, the ratio of pyridine to picolines is not suitable, and the yield of the desired pyridine product decreases sharply after several reaction/regeneration cycles.

In view of the above considerations, it is clear that existing processes for synthesis of pyridines, picolines, and related compounds is encumbered by disadvantages that render the processes unacceptable from a commercial perspective. Specifically, (1) large amounts of carbonaceous deposits form which reduce the activity of the catalyst to below acceptable levels; (2) the selectivity of the reaction for the desired pyridine and alkylpyridine becomes very poor; (3) the catalysts become thermally unstable; and (4)

the activity of the used catalyst is difficult to restore completely by regeneration.

Accordingly, it is one of the purposes of this invention to overcome the above limitations in pyridine and picoline synthetic processes, by providing a process by which high yields and high purities of desirable products can be achieved in a cost- and time-efficient manner. It is a further purpose of this invention to provide a pyridine synthesis process that can be readily adapted and scaled to commercial application.

SUMMARY OF THE INVENTION

It has now been discovered that these and other objectives can be achieved by the present invention, which provides a method for preparing pyridines or picolines from a base synthesis reaction over a molecular sieve catalyst, separating the heavier products from this reaction, and then converting the heavier components to additional pyridines or picolines.

In one embodiment, the invention is a process for shape selective base synthesis of pyridine or picoline compounds, comprising:

(a) reacting a reactant feedstream comprising ammonia and at least one $C_{1-5}$ carbonyl reactant under suitable synthesis reaction conditions of temperature, pressure, and space velocity in the presence of a catalyst comprising a molecular sieve to produce a primary product stream comprising pyridine or picoline products and polyalkylpyridines or higher molecular weight species;

(b) isolating from the primary product stream a product fraction comprising pyridine or picoline products, and a polyalkylpyridine fraction comprising polyalkylpyridines or other higher molecular weight aromatic species; and (c) converting the polyalkylpyridine fraction under suitable conversion reaction conditions of temperature, pressure, and space velocity in the presence of a catalyst comprising a molecular sieve to produce a secondary product stream comprising pyridine or picoline products, whereby the net amount of polyalkylpyridines or other higher molecular weight aromatic species in the polyalkylpyridine fraction and the secondary product stream are substantially reduced relative to the amount in the primary product stream.

In the process the synthesis reaction conditions and the conversion reaction conditions can each be determined independently, and generally comprise a temperature of from about 285° C. to about 600° C.; a pressure of from about 0.2 atm to about 20 atm; and a gas hourly space velocity (GHSV) of from about 200 $hr^{-1}$ to about 20,000 $hr^{-1}$. Alternatively, the synthesis reaction conditions and the conversion reaction conditions can comprise a temperature of from about 340° C. to about 550° C.; a pressure of from about 0.8 atm to about 10 atm; and a GHSV of from about 300 $hr^{-1}$ to about 5,000 $hr^{-1}$.

The molecular sieve of the catalyst can be selected from the group consisting of ZSM-5, ZSM-11, ZSM-12, ZSM-21, ZSM-22, ZSM-23, ZSM-35, ZSM-38, ZSM-48, ZSM-57, ZSM-58, S-115, MCM-22, MCM-36, MCM-49, MCM-56, SAPO-5, SAPO-11, zeolite Beta, zeolite X, zeolite Y, and the like. Preferably, the molecular sieve has a Constraint Index of from about 1 to about 12.

The process can be performed using a mole ratio of the ammonia to the at least one carbonyl reactant in the reactant feedstream is from about 0.5 to about 10. Alternatively, the mole ratio of the ammonia to the at least one carbonyl reactant in the reactant feedstream can be from about 1 to about 5.

Preferably, the at least one carbonyl reactant consists at least essentially of acetaldehyde and formaldehyde. In such cases, the formaldehyde/acetaldehyde mole ratio is from about 0.2 to about 1.0, preferably from about 0.4 to about 0.8.

A particularly preferred feedstream for use according to the process of the invention consists at least essentially of 1.4 parts acetaldehyde; 1.0 parts formaldehyde; 3.6 parts ammonia; and 1.6 parts hydrogen, on a molar basis.

The process can be performed with co-feeding of hydrogen with the reactant feedstream, wherein the mole ratio of the hydrogen to the at least one carbonyl reactant in the reactant feedstream is from 0 to about 5.0. The mole ratio of the hydrogen to the at least one carbonyl reactant in the reactant feedstream can be from about 0.1 to about 1.0.

The process of the invention can substantially reduce the net make of polyalkylpyridines or higher molecular weight aromatic hydrocarbon species. Thus, the net amount of these by-products in the product fraction and the secondary product stream together comprises less than about 5 wt % of the yield. More preferably, the net amount of polyalkylpyridines and higher molecular weight aromatic species in the product fraction and the secondary product stream together comprise less than about 2 wt % of the yield.

Optionally, the converting step (c) comprises recirculating the polyalkylpyridine fraction to the catalyst used for the reacting step (a), and wherein the conversion is accomplished under the synthesis reaction conditions of the reacting step (a).

The isolating step (b) can comprise fractional distilling the primary product stream to permit collection of the product fraction and the polyalkylpyridine fraction.

In another embodiment, the invention is a process which comprises reacting ammonia and at least one $C_{1-5}$ carbonyl reactant under suitable reaction conditions of temperature, pressure, and space velocity in the presence of a catalyst comprising a molecular sieve to produce a primary product stream comprising pyridine or picoline products and polyalkylpyridines or other higher molecular weight aromatic species, wherein the process comprises steps of:

(a) isolating from the primary product stream a primary product fraction comprising the pyridine or picoline products, and a polyalkylpyridine fraction comprising polyalkylpyridines or other higher molecular weight aromatic species; and (b) recirculating the polyalkylpyridine fraction to the catalyst to convert polyalkylpyridines or other higher molecular weight aromatic species therein under the reaction conditions to produce a secondary product comprising pyridine or picoline products and a substantially reduced amount of polyalkylpyridines or other higher molecular weight aromatic species relative to the amount in the primary product stream.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE PREFERRED EMBODIMENTS

As mentioned hereinabove, the term "base synthesis" is known and used in the field of pyridine chemistry (and will be used in this application) to identify synthetic processes by which bases of pyridine or alkylpyridine derivatives are prepared by reacting aldehydes and/or ketones with ammonia in the gas phase using a heterogeneous catalyst. Some examples of base synthesis reactions suitable for use in the method of the invention include:

the synthesis of pyridine and beta-picoline from acetaldehyde and formaldehyde (the "pyridine-beta reaction");

the synthesis of alpha- and gamma-picoline from acetaldehyde (the "alpha-gamma reaction");

the synthesis of 2,6-dimethylpyridine (2,6-lutidine) from acetone and formaldehyde;

the synthesis of 2,4,6-trimethylpyridine (sym-collidine) from acetone alone or with acetaldehyde;

the synthesis of pyridine and β-picoline from acrolein alone or with acetaldehyde;

the synthesis of 3,5-dimethylpyridine from propionaldehyde and formaldehyde; and the synthesis of beta-picoline from acetaldehyde, formaldehyde, and propionaldehyde.

In a highly preferred embodiment, base synthesis means the pyridine-beta reaction, i.e., the synthesis of pyridine and β-picoline from acetaldehyde and formaldehyde. Many other reaction types suitable for use according to the claimed invention are known and practiced in the art.

The carbonyl reactant used in the base synthesis reaction is a hydrocarbon compound containing 1 to 5 carbon atoms ($C_{1-5}$) and at least one carbonyl moiety (C=O) within that structure. The carbonyl reactant taking part in the catalytic reaction described herein may be formaldehyde, an aldehyde containing 2 to 4 carbon atoms ($C_{2-4}$ aldehyde), a ketone containing 3 to 5 carbon atoms ($C_{3-5}$ ketone), or mixtures thereof. Representative reactant aldehydes include acetaldehyde, propionaldehyde, acrolein, butyraldehyde, and crotonaldehyde. Representative reactant ketones include acetone, methyl ethyl ketone, diethyl ketone, and methyl propyl ketone. The carbonyl reactant can be present as a solution in water, e.g., formalin which is a solution of formaldehyde in water, with a small amount of methanol to aid solubility.

The carbonyl reactant may comprise a mixture of two or more carbonyl compounds. If a mixture is used, each carbonyl component in the mixture is preferably present in a predetermined amount relative to the other carbonyl components. For example, when the at least one carbonyl reactant is a mixture of formaldehyde and acetaldehyde, the two components are present in a formaldehyde/acetaldehyde mole ratio of from about 0.2 to about 1.0, preferably from about 0.4 to about 0.8. Alternatively, mixtures of acetaldehyde and acrolein will typically have an acetaldehyde/acrolein mole ratio of from about 0.7 to about 1.25. The artisan will appreciate that other mixtures of carbonyl reactants can be similarly formulated to selectively control the product of the base synthesis.

The mole ratio of ammonia to carbonyl reactant ($NH_3$/CO) in the reaction mixture employed will generally be between about 0.5 to about 30, preferably between about 0.5 and about 10, and more preferably between about 1 and about 5.

Hydrogen gas ($H_2$) may, if desired, be added to the reaction, e.g., at the rate of from 0 (no added hydrogen) to an $H_2$/carbonyl reactant ($H_2$/CO) mole ratio of about 5.0, preferably from about 0.1 to about 1.0.

At the completion of the base synthesis reaction, the recovered product may be separated into its desired components by any feasible means, e.g., by fractionation, to recover a product containing the pyridine or the 3-alkylpyridine compound. Of the 3-alkylpyridine compounds selectively produced by way of the present invention, 3-picoline is an important intermediate in the manufacture of 3-pyridinecarboxylic acid, i.e., nicotinic acid, and other medicinal, agricultural, and chemical products. These products have important pharmaceutical significance as well as being used as additives in food and feeds. Another of the compounds selectively produced by way of the present invention is pyridine. This latter compound is an important chemical used in the manufacture of herbicides and pesticides. It is also used as a solvent in the textile industry. Accordingly, the process of the invention can be further modified to accommodate the synthesis of 3-pyridinecarboxylic acid, by recovering the 3-picoline product and contacting the recovered 3-picoline with an oxidative reagent such as $KMnO_4$.

The process of the invention finds an important advantage in that the make of polyalkylpyridines and/or other higher molecular weight aromatic species is substantially reduced as compared to conventional processes. This feature is accompanied by an increase in the yield of the desired pyridine or picoline products.

By "polyalkylpyridine by-products" is meant pyridine derivatives having two or more alkyl groups attached to the ring structure. Such compounds are exemplified by lutidine and collidine. In a conventional single-pass reaction, these polyalkylpyridine by-products, as well as other higher molecular weight aromatic species are produced in amounts of up to 20 wt % or more, which makes such processes highly inefficient. The process of the invention, by contrast, has been found to reduce the total make of polyalkylpyridines and higher molecular weight aromatic species to less than about 5 wt %, often less than about 2 wt %, and usually less than about 1 wt %. By the same token the total yield of pyridine and picoline products is significantly increased using the process of the invention as contrasted against conventional base synthesis processes.

Thus, the fractionation of the product of the base synthesis reaction can yield a product fraction, comprising the pyridine or picoline products, and a polyalkylpyridine fraction, comprising polyalkylpyridine by-products and/or other higher molecular weight aromatic or alkylated aromatic species. The term "polyalkylpyridine fraction" means a fraction of the primary product that comprises a substantial amount of polyalkylpyridines per se, but may further comprise higher molecular weight aromatic compounds, such as alkylated polynuclear aromatic structures related to the pyridines. The polyalkylpyridine fraction may be defined as that fraction derived from the primary product that is subjected to a secondary reaction as described herein to convert the polyalkylpyridines or higher molecular weight aromatic species to pyridines or picolines.

The reaction conditions for performing the base synthesis reaction between the ammonia and the at least one carbonyl compound include:

(a) Temperature of from about 285° C. to about 600° C., preferably from about 340° C. to about 550° C.;

(b) Pressure of from about 0.2 atm to about 20 atm, preferably from about 0.8 atm to about 10 atm; and (c) Gas hourly space velocity (GHSV) of from about 200 $hr^{-1}$ to about 20,000 $hr^{-1}$, preferably from about 300 $hr^{-1}$ to about 5,000 $hr^{-1}$.

The reaction conditions for performing the secondary reaction to convert the polyalkylpyridines or other higher molecular weight aromatic species in the polyalkylpyridine fraction to secondary product enriched for pyridine or picoline products are in the same approximate ranges as those for the base synthesis reaction.

The reaction may proceed in a fixed bed, moving bed, or fluidized bed reactor. A fluidized bed reactor is preferred, as, among other advantages, this type of reactor facilitates catalyst regeneration.

It should be recognized that, while the present description provides details about a recycling process, where a fraction of reactor effluent is recycled to the reactor for a secondary reaction, it is within the scope of the invention to use two reactors in series. In such a scenario, the primary reactor receives the carbonyl reactant with the ammonia, and the second reactor receives the polyalkylpyridine fraction. Pyridine and picoline product is recovered in two stages, i.e., a primary fraction from the first reactor and a secondary fraction from the second reactor. The catalyst in each of the first and second reactors, and the conversion conditions in each of the reactors, may be the same or different as desired to accomplish specific purposes such as controlling the proportions of pyridine and picolines (as well as the amounts of by-products) in the reactor effluents.

Catalyst System

The base synthesis reaction and the polyalkylpyridine conversion reactions are performed over a catalyst comprising a synthetic porous crystalline material. Preferred catalyst materials comprise zeolites, such as ZSM-5, prepared with binder materials as further described hereinbelow.

The alpha value of the catalyst should be at least 5. The catalyst of the present invention preferably has an alpha value greater than 100, for example, from about 150 to about 2000. The alpha value is an approximate indication of the catalytic cracking activity of the catalyst compared to a standard catalyst and it gives the relative rate constant (rate of normal hexane conversion per volume of catalyst per unit time.) It is based on the activity of an amorphous silica-alumina cracking catalyst taken as an alpha of 1 (Rate Constant=0.016 sec$^{-1}$). The Alpha Test is described in U.S. Pat. No. 3,354,078 and in J. Catalysis 4:522–529 (August 1965): J. Catalysis 6:278 (1966); and J. Catalysis 61:395 (1980), each incorporated herein by reference as to that description. It is noted that intrinsic rate constants for many acid-catalyzed reactions are proportional to the alpha value for a particular crystalline silicate catalyst (see "The active site of acidic aluminosilicate catalysts," Nature, 309(5959):589–591, (Jun. 14, 1984)). The alpha value of the catalyst may be increased by treating the catalyst with nitric acid or by mild steaming as discussed in U.S. Pat. Nos. 3,257,310 and 4,326,994.

The parent molecular sieve component of this catalyst may be one characterized by a Constraint Index within the approximate range of 1 to 12. The method by which Constraint Index is determined is described in U.S. Pat. No. 4,016,218, incorporated herein by reference. This parameter embraces a number of molecular sieves, as otherwise described herein.

Accordingly, catalysts useful in this invention comprise a catalytic molecular sieve. The molecular sieve is preferably a zeolite having at least an intermediate pore size. Zeolites having a larger pore size may be more preferred. Examples of intermediate pore size zeolites useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-21 (U.S. Pat. No. 4,046,859); ZSM-22 (U.S. Pat. No. 4,556,447); ZSM-23 (U.S. Pat. No. 4,076,842); ZSM-35 (U.S. Pat. No. 4,016,245); ZSM-38 (U.S. Pat. No. 4,406,859); ZSM-48 (U.S. Pat. No. 4,397,827); ZSM-57 (U.S. Pat. No. 4,046,685); and ZSM-58 (U.S. Pat. No. 4,417,780). Methods used to prepare controlled crystal size ZSM-5 are described, for example, in U.S. Pat. Nos. 4,117,026; 4,526,879; and 4,899,011; 3,702,886; 4,175,114; 4,199,556; 4,341,748; 4,375,458; 5,182,090; 5,243,117; and Great Britain Pat. No. 1,581,513, the disclosures of which are incorporated herein by reference. ZSM-5 zeolites are particularly preferred.

Other useful catalyst materials include those described in U.S. Pat. No. 4,992,606. U.S. Pat. No. 5,236,575 describes MCM-49 another synthetic crystalline material useful as a catalyst component for the present process. U.S. Pat. No. 5,218,122 describes the use of a catalyst designated S-115 in pyridine base synthesis reactions, which is also suitable for use according to the process of the invention. Moreover, U.S. Pat. No. 5,395,940 describes MCM-22, which is another synthetic porous crystalline material useful as a catalyst in the process of the invention. Each of these patents is incorporated herein by reference. MCM-36, MCM-49, MCM-56, SAPO-5, SAPO-11, zeolite X, zeolite Y, and zeolite Beta are also examples of molecular sieve materials that can also be used according to the invention. In any event, while much of the discussion herein may be directed to ZSM-5 zeolites, the artisan will recognize that similar considerations apply to other molecular sieves.

Larger pore size materials may have as an advantage a capacity for converting bulkier molecules in the processing system according to the invention. Such larger pore materials include, for example, MCM-22, zeolite Beta, zeolite Y, ZSM-20, and the like.

The molecular sieve also has a silica to alumina ($SiO_2$/$Al_2O_3$) molar ratio of at least about 5, preferably from about 12 to about 100, and more preferably from about 20 to about 80. The silica to alumina ratio referred to may be determined by conventional analysis, such as elemental analysis or nuclear magnetic resonance spectroscopy. This ratio is meant to represent, as closely as possible, the molar ratio in the rigid anionic framework of the molecular sieve crystal and to exclude silicon and aluminum in the binder or in cationic or other form within the channels.

The catalyst may be characterized according to its xylene diffusion or xylene sorption properties. In particular, it has been found that the catalyst should possess an equilibrium sorption capacity of xylene, which can be either para-, meta-, ortho-, or a mixture thereof, frequently para-xylene, since this isomer reaches equilibrium within the shortest time, of at least 1 g per 100 g of molecular sieve measured at 120° C. and a xylene pressure of 4.5±0.8 mm of mercury (493 Paa to 707 Paa), and an ortho-xylene sorption ($t_{0.3}$), i.e., the time required to achieve 30% of the xylene sorption capacity, of greater than 50 minutes (at the same conditions of temperature and pressure) to achieve the desired level of ethylbenzene conversion while maintaining the desired level of xylene loss. The sorption measurements may be carried out gravimetrically in a thermal balance. The sorption test is described in U.S. Pat. Nos. 4,117,026; 4,159,282; 5,173,461; and Re. 31,782, each incorporated herein by reference.

The suitable molecular sieve may be employed in combination with a support or binder material such as, for example, a porous inorganic oxide support or a clay binder. For example, it may be desirable to formulate the catalyst of the invention with another material resistant to the temperature and other conditions of the hydrocarbon conversion process. Illustrative examples of binder materials include synthetic or naturally occurring substances as well as inorganic materials such as clay, silica, and/or metal oxides, such as alumina, vanadia, beryllia, thoria, magnesia, titania, zirconia, boria, and combinations thereof. The preferred binder is primarily silica. The metal oxides may be naturally occurring or in the form of gelatinous precipitates or gels including mixtures of silica and metal oxides.

Naturally occurring clays that can be composited with the molecular sieve include those of the montmorillonite and kaolin families, which families include the subbentonites and the kaolins commonly known as Dixie, McNamee, Georgia, and Florida clays, or others in which the main mineral constituent is halloysite, kaolinite, dickite, nacrite, or anauxite. Suitable clay materials include, by way of example, bentonite and kieselguhr. Such clays can be used in the raw state as originally mined or initially subjected to calcination, acid treatment, or chemical modification.

The relative proportion of suitable crystalline molecular sieve to the total composition of catalyst and binder or support may be from about 1 wt % to about 99 wt %, preferably from about 30 wt % to about 90 wt %, and more preferably from about 50 wt % to about 80 wt %, of the composition.

The form and the particle size of the catalyst are not critical to the present invention and may vary depending, for example, on the type of reaction system employed. Non-limiting examples of the shapes of the catalyst in the present invention include balls, pebbles, spheres, extrudates, channeled monoliths, honeycombed monoliths, microspheres, pellets, or structural shapes, such as lobes, trilobes, quadralobes, pills, cakes, honeycombs, powders, granules, and the like, formed using conventional methods, such as extrusion or spray drying.

Exemplary procedures for preparing silica bound molecular sieves are described in U.S. Pat. Nos. 4,582,815; 5,053,374; and 5,182,242. For example, a procedure for binding a molecular sieve involves an extrusion process. Thus, a silica-bound molecular sieve may be prepared by a process comprising the steps of:

(a) mulling and then extruding a mixture comprising water, a molecular sieve, colloidal silica and sodium ions under conditions sufficient to form an extrudate having an intermediate green strength sufficient to resist attrition during ion exchange step (b) set forth hereinafter;

(b) contacting the extrudate of step (a) with an aqueous solution comprising ammonium cations under conditions sufficient to exchange cations in the molecular sieve with ammonium cations; and (c) calcining the ammonium exchanged extrudate of step (b) under conditions sufficient to generate a hydrogen form of the molecular sieve and increase the crush strength of the extrudate.

Another method of silica binding uses a suitable silicone resin, e.g., a high molecular weight, hydroxy functional silicone resin, in a method disclosed in U.S. Pat. Nos. 4,631,267 and 3,090,691. Extrusion aids, such as methyl cellulose materials may also be useful in the preparation of the catalysts of this invention.

The molecular sieve, either directly or via initial ammonium exchange followed by calcination, may be hydrogen exchanged such that a predominant proportion of its exchangeable cations are hydrogen ions. It is contemplated that more than 50% and preferably more than 75% of the cationic sites of the crystalline aluminosilicate molecular sieve will be occupied by hydrogen ions.

Original ions, e.g., alkali or alkaline earth metal, of the as-synthesized molecular sieve can be replaced in accordance with techniques well known in the art, at least in part, by ion exchange with other ions. Typical ion exchange techniques would be to contact the synthetic molecular sieve with a solution containing a salt of the desired replacing ion or ions. Examples of such salts include the halides, e.g., chlorides, nitrates, and sulfates. Representative ion exchange techniques are disclosed in a wide variety of patents including U.S. Pat. Nos. 3,140,251 and 3,140,253, each incorporated herein by reference.

A hydrogenation-dehydrogenation functional metal can be incorporated into the catalyst of the invention. Such metals are known in the art to reduce ethylbenzene by-product in hydrocarbon conversion processes. See, e.g., U.S. Pat. No. 5,498,814, incorporated herein by reference.

Any metal possessing the desired hydrogenation-dehydrogenation function can be used in the modification method of the invention. These are termed "functional metals." Examples of such functional metals include the oxide, hydroxide, sulfide, or free metal (i.e., zero valent) forms of metals in the Groups 3 to 15 of the periodic table. Preferred metals include Group 8, 9, and 10 metals (i.e., Pt, Pd, Ir, Rh, Os, Ru, Ni, Co, and Fe), Group 7 metals (i.e., Mn, Tc, and Re), Group 6 metals (i.e., Cr, Mo, and W), Group 15 metals (i.e., Sb and Bi), Group 14 metals (i.e., Sn and Pb), Group 13 metals (i.e., Ga and In), Group 11 metals (i.e., Cu, Ag, and Au), and Group 12 metals (i.e., Zn, Cd, and Hg). Noble metals (i.e., Pt, Pd, Ir, Rh, Os, Re, Ru, Mo, and W) are preferred. U.S. Pat. No. 4,866,179, incorporated herein by reference, describes modification of a catalyst by incorporation of a Group 8, 9, or 10 (Group VIII) metal to improve performance in pyridine synthesis reactions.

Combinations or mixtures of catalytic forms of such noble or non-noble metal, such as combinations of Pt with Sn, may be used. The valence state of the metal is preferably reduced, e.g., when this component is in the form of an oxide or hydroxide. The reduced valence state of the functional metal may be attained, in situ, during the course of a reaction, when a reducing agent, such as hydrogen, is included in the feed to the reaction.

The functional metal may be incorporated into the catalyst by methods known in the art, such as ion exchange, impregnation, or physical admixture. For example, solutions of appropriate metal salts may be contacted with the remaining catalyst components under conditions sufficient to combine the respective components. The metal-containing salt is preferably water-soluble. Examples of such salts include chloroplatinic acid, tetraammine platinum complexes, platinum chloride, tin sulfate, and tin chloride. The metal may be incorporated in the form of a cationic, anionic, or neutral complex such as $Pt(NH_3)_4^{2+}$, and cationic complexes of this type will be found convenient for exchanging metals into the molecular sieve. Anionic complexes such as the vanadate or metatungstate ions are also useful for impregnating metals into the molecular sieves. Incorporation is preferably undertaken in accordance with the method described in U.S. Pat. No. 4,312,790. After incorporation of the metal, the catalyst can then be filtered, washed with water, and calcined at temperatures of from 250° C. to 500° C.

The functional metal is preferably able to enter the pores of the catalyst, i.e., permeate into the catalyst, to be able to survive high temperature exposure, such as that associated with calcination or conversion conditions. Addition of the metal can be accomplished through mixing the catalyst with a solution, preferably aqueous, of an appropriate metal salt, acid, oxide, or other metal complex. The mixing can be performed at about ambient temperature or at elevated temperatures, e.g., through reflux. In certain circumstances several exchanges may be required to facilitate proper permeation of the desired metal. For example, in the case of an acidic form of a catalyst it may be desirable to perform a first exchange to provide an ammonium form, followed by a second exchange to provide the metal form.

The amount of functional metal may be that amount which increases the catalytic ability of the overall catalyst to catalytically hydrogenate or dehydrogenate an organic compound, e.g., ethylene, under sufficient hydrogenation or dehydrogenation conditions. This amount is referred to herein as a catalytic amount. The amount of the functional metal is suitably from about 0.001 wt % to 10 wt %, preferably from about 0.05 wt % to about 5 wt %, more preferably from about 0.1 wt % to about 2 wt %, based on the total weight of the modified catalyst. However the artisan will recognize that the required amount of the functional metal will vary with the nature of the component, with less of the highly active noble metals being required than of the less active base metals.

The catalyst may be subjected to steaming conditions sufficient to increase or decrease the activity and/or selectivity of the catalyst as desired. Such conditions are disclosed, for example, in U.S. Pat. No. 5,349,114. The steaming conditions may include a temperature of from about 100° C. to about 800° C., e.g., from about 175° C. to about 325° C., with from about 1% to about 100% steam, e.g., from about 50% to about 100% steam, at a pressure of from about 0.01 psia (69 Paa) to about 5000 psia (34474 kPaa), and for a duration of from about 0.1 hr to about 24 hr, e.g., from about 3 hr to about 6 hr. Excessive steaming or steaming under severe conditions may be detrimental to the activity and selectivity of the catalyst.

The present catalyst may comprise at least 0.03 wt %, e.g., at least 0.1 wt %, of alkali metal or alkaline earth metal, e.g., an amount effective to achieve the desired activity/selectivity. Particular alkali metals include Li, Na, K, Rb, and Cs. Particular alkaline earth metals include Mg, Ca, Sr, and Ba. The alkali metal or alkaline earth metal may be added by contacting the catalyst, in particular, the molecular sieve component of the catalyst, with an aqueous solution containing an alkali metal, ion of an alkali metal, alkaline earth metal, or ion of an alkaline earth metal, optionally washing off excess solution using water or another solvent, and then drying the treated catalyst. The present alkali metal or alkaline earth metal incorporation or ion exchange procedure may be used to decrease the activity of the catalyst. The activity may be adjusted on a small scale to fine-tune batches of the catalyst for a particular use or the activity may be adjusted on a major scale to convert the catalyst from one type to another, thereby providing a means to manufacture different catalysts for different uses. The amount of alkali metal or alkaline earth metal ions incorporated into the catalyst will generally negatively affect catalyst activity, and can be selected as desired to fine-tune the activity of the catalyst. Thus, smaller amounts of alkali metal or alkaline earth metal will reduce the alpha value of the catalyst by a smaller amount, e.g., about 10%, and larger amounts of alkali metal or alkaline earth metal will reduce the alpha value of the catalyst by a larger amount, e.g., by 50% or more.

The following examples are provided to assist in a further understanding of the invention. The particular materials and conditions employed are intended to be further illustrative of the invention and are not limiting upon the reasonable scope thereof.

EXAMPLE 1

A base synthesis reaction to produce pyridine and picoline products is performed. The catalyst is a 40% HZSM-5 zeolite spray-dried in a silica-alumina-clay matrix. Final catalyst activity is adjusted by steaming. In a typical run, 5–10 mL of 20/40 mesh catalyst is charged to a quartz reactor and heated to 440–454° C. (825–850° F.) under an $N_2$ purge. The feed consists of acetaldehyde, formaldehyde, ammonia, and hydrogen in the following molar ratios: acetaldehyde=1.4; formaldehyde=1.0; ammonia=3.6; hydrogen=1.6. The feed is passed over the catalyst at 580 $hr^{-1}$ GHSV ($NH_3$), and the effluent is analyzed by gas chromatography (GC) using quinoline as an internal standard. Water content in the product is determined by Karl-Fischer titration. The yields of the various products of this reaction are given in Table 1.

EXAMPLE 2

The pyridine and picoline products in the effluent of the reaction described in Example 1 are distilled off and collected, and the aqueous layer is removed. The heavier N-containing components are recycled back into the reactor. Additional catalyst is added as needed to increase the conversion of polymethylpyridines. The yields of the various products following this reaction are given in Table 1.

TABLE 1

|  | Example 1 (No Recycle) | Example 2 (With Recycle) |
| --- | --- | --- |
| Temperature (° C.) | 440 | 440 |
| Catalyst Charge (mL) | 5.0 | 7.0 |
| Run Time (min) | 120 | 120 |
| Acetaldehyde Conversion (%) | 85.9 | 86 |
| Formaldehyde Conversion (%) | 79.1 | 80 |
| Yield of N-Products[1] (%) | 43.1 | 43 |
| Selectivities (%) |  |  |
| Pyridine | 38.7 | 50 |
| Picoline | 22.1 | 30 |
| Polyalkylpyridines | 18.1 | <1 |
| Higher MW Products, tars, etc. | 21.1 | 20 |

[1]Wt N-containing products/wt acetaldehyde feed

Table 1 clearly illustrates that the process of the invention (Example 2) can substantially increase the process selectivity for pyridine and picolines as compared to the prior art single pass process (Example 1). Polyalkylpyridine by-product yield is substantially reduced, from 18.1% to less than 1%. Note that, for comparison purposes, the acetaldehyde conversions for each example are accomplished by increasing the catalyst charge to the reactor. Accordingly, the process of the invention achieves a substantial increase in efficiency on the basis of the total yield of pyridine and picoline products from a given amount of feed.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A process for shape selective base synthesis of pyridine or picoline compounds, comprising:
   (a) reacting a reactant feedstream comprising ammonia and at least one $C_{1-5}$ carbonyl reactant under suitable synthesis reaction conditions of temperature, pressure, and space velocity in the presence of a catalyst comprising a molecular sieve to produce a primary product stream comprising pyridine or picoline products and polyalkylpyridines or higher molecular weight species;

(b) separating from the primary product stream a product fraction comprising pyridine or picoline products, and a polyalkylpyridine fraction comprising polyalkylpyridines or other higher molecular weight aromatic species; and (c) recirculating the polyalkylpyridine fraction to the catalyst to convert polyalkylpyridines or other higher molecular weight aromatic species therein under the reaction conditions to produce a secondary product comprising pyridine or picoline products and less than about 5 wt % polyalkylpyridines or other higher molecular weight aromatic species.

2. A process according to claim 1, wherein the synthesis reaction conditions comprise a temperature of from about 285° C. to about 600° C.; a pressure of from about 0.2 atm to about 20 atm; and a GHSV of from about 200 $hr^{-1}$ to about 20,000 $hr^{-1}$.

3. A process according to claim 1, wherein the synthesis reaction conditions comprise a temperature of from about 340° C. to about 550° C., a pressure of from about 0.8 atm to about 10 atm; and a GHSV of from about 300 $hr^{-1}$ to about 5,000 $hr^{-1}$.

4. A process according to claim 1, wherein the molecular sieve is selected from the group consisting of ZSM-5, ZSM-11, ZSM-12, ZSM-21, ZSM-22, ZSM-23, ZSM-35, ZSM-38, ZSM-48, ZSM-57, ZSM-58, S-115, MCM-22, MCM-36, MCM-49, MCM-56, SAPO-5, SAPO-11, zeolite Beta, zeolite X, and zeolite Y.

5. A process according to claim 1, wherein the molecular sieve has a Constraint Index of from about 1 to about 12.

6. A process according to claim 1, wherein the mole ratio of the ammonia to the at least one carbonyl reactant in the reactant feedstream is from about 0.5 to about 10.

7. A process according to claim 6, wherein the mole ratio of the ammonia to the at least one carbonyl reactant in the reactant feedstream is from about 1 to about 5.

8. A process according to claim 1, wherein the at least one carbonyl reactant consists essentially of acetaldehyde and formaldehyde.

9. A process according to claim 8, wherein the formaldehyde/acetaldehyde mole ratio is from about 0.2 to about 1.0.

10. A process according to claim 9, wherein the formaldehyde/acetaldehyde mole ratio is from about 0.4 to about 0.8.

11. A process according to claim 1, wherein the reactant feedstream consists essentially of 1.4 parts acetaldehyde; 1.0 parts formaldehyde; 3.6 parts ammonia; and 1.6 parts hydrogen, on a molar basis.

12. A process according to claim 1, further comprising co-feeding hydrogen with the reactant feedstream wherein the mole ratio of the hydrogen to the at least one carbonyl reactant in the reactant feedstream is from 0 to about 5.0.

13. A process according to claim 12, wherein the mole ratio of the hydrogen to the at least one carbonyl reactant in the reactant feedstream is from about 0.1 to about 1.0.

14. A process according to claim 1, wherein the secondary product stream comprises less than about 2 wt % polyalkylpyridines or other higher molecular weight aromatic species.

15. A process according to claim 1, wherein the separating step (b) comprises fractional distilling the primary product stream to permit collection of the product fraction and the polyalkylpyridine fraction.

* * * * *